United States Patent
Erskine

(10) Patent No.: US 9,278,195 B2
(45) Date of Patent: Mar. 8, 2016

(54) NEEDLE SHIELD ASSEMBLY WITH HUB ENGAGEMENT MEMBER FOR NEEDLE DEVICE

(75) Inventor: Timothy J. Erskine, Sister Bay, WI (US)

(73) Assignee: Erskine Medical LLC, High Falls, NY (US)

( * ) Notice: Subject to any disclaimer, the term of this patent is extended or adjusted under 35 U.S.C. 154(b) by 297 days.

(21) Appl. No.: 13/997,969

(22) PCT Filed: Dec. 2, 2011

(86) PCT No.: PCT/US2011/063081
§ 371 (c)(1),
(2), (4) Date: Jun. 25, 2013

(87) PCT Pub. No.: WO2012/075402
PCT Pub. Date: Jun. 7, 2012

(65) Prior Publication Data
US 2013/0296805 A1    Nov. 7, 2013

Related U.S. Application Data

(60) Provisional application No. 61/418,997, filed on Dec. 2, 2010.

(51) Int. Cl.
*A61M 25/06* (2006.01)
*A61B 5/15* (2006.01)
*A61M 5/32* (2006.01)

(52) U.S. Cl.
CPC ...... *A61M 25/0631* (2013.01); *A61B 5/150633* (2013.01); *A61M 5/3243* (2013.01); *A61M 2005/325* (2013.01)

(58) Field of Classification Search
CPC .......... A61M 25/0631; A61M 5/3243; A61M 2005/3247; A61B 5/150633
See application file for complete search history.

(56) References Cited

U.S. PATENT DOCUMENTS 2,798,487 A    7/1957   Ferguson
3,459,183 A    8/1969   Ring et al.
(Continued)

FOREIGN PATENT DOCUMENTS

CN    1145813 A    3/1997
CN    1547493 A    11/2004
(Continued)

OTHER PUBLICATIONS

European Patent Office, Supplementary European Search Report for EP09842422 dated Aug. 27, 2012, 7 pages.
(Continued)

*Primary Examiner* — Laura Bouchelle
(74) *Attorney, Agent, or Firm* — Hoffman Warnick LLC

(57) ABSTRACT

A passively activated needle shield assembly with a hub engagement member for a needle device is provided. The needle shield assembly includes a needle shield movable between a non-shielding position and a shielding position. The needle shield prevents emergence of a sharp distal end of a needle therefrom in the shielding position. An engagement member is slidingly disposed relative to the needle shield for engaging the hub to the needle shield in the non-shielding position. A retainer operatively couples to the engagement member and is positioned to prevent disengagement of the engagement member from the hub in the non-shielding position, and enables removal of the hub from the needle shield by disengaging the engagement member from the hub when the needle shield moves to the shielding position.

22 Claims, 6 Drawing Sheets

(56) References Cited

U.S. PATENT DOCUMENTS

| | | |
|---|---|---|
| 4,588,398 A | 5/1986 | Daugherty et al. |
| 4,596,563 A | 6/1986 | Pande |
| 4,755,170 A | 7/1988 | Golden |
| 4,762,516 A | 8/1988 | Luther et al. |
| 4,778,453 A | 10/1988 | Lopez |
| 4,790,828 A | 12/1988 | Dombrowski et al. |
| 4,832,696 A | 5/1989 | Luther et al. |
| 4,834,718 A | 5/1989 | McDonald |
| 4,846,809 A | 7/1989 | Sims |
| 4,863,436 A | 9/1989 | Glick |
| 4,887,998 A | 12/1989 | Martin et al. |
| 4,927,414 A | 5/1990 | Kulli |
| 4,929,241 A | 5/1990 | Kulli |
| 4,931,048 A | 6/1990 | Lopez |
| 4,944,725 A | 7/1990 | McDonald |
| 4,952,207 A | 8/1990 | Lemieux |
| 4,978,344 A | 12/1990 | Dombrowski et al. |
| 5,049,136 A | 9/1991 | Johnson |
| 5,059,180 A | 10/1991 | McLees |
| 5,116,326 A | 5/1992 | Schmidt |
| 5,120,320 A | 6/1992 | Fayngold |
| 5,160,325 A | 11/1992 | Nichols et al. |
| 5,215,528 A | 6/1993 | Purdy et al. |
| RE34,416 E | 10/1993 | Lemieux |
| 5,261,895 A | 11/1993 | Kablik |
| 5,300,045 A | 4/1994 | Plassche, Jr. |
| 5,304,151 A | 4/1994 | Kuracina |
| 5,322,517 A | 6/1994 | Sircom et al. |
| 5,328,482 A | 7/1994 | Sircom et al. |
| 5,334,158 A | 8/1994 | McLees |
| 5,344,408 A | 9/1994 | Partika |
| 5,360,408 A | 11/1994 | Vaillancourt |
| 5,360,497 A | 11/1994 | Schneider et al. |
| 5,376,075 A | 12/1994 | Haughton et al. |
| 5,429,611 A | 7/1995 | Rait |
| 5,447,501 A | 9/1995 | Karlsson et al. |
| 5,458,658 A | 10/1995 | Sircom |
| 5,466,223 A | 11/1995 | Bressler et al. |
| 5,558,651 A | 9/1996 | Crawford et al. |
| 5,582,597 A | 12/1996 | Brimhall et al. |
| 5,584,809 A | 12/1996 | Gaba |
| 5,599,310 A | 2/1997 | Bogert |
| 5,601,536 A | 2/1997 | Crawford et al. |
| 5,611,781 A | 3/1997 | Sircom et al. |
| 5,662,610 A | 9/1997 | Sircom |
| 5,669,927 A | 9/1997 | Boebel et al. |
| 5,683,365 A | 11/1997 | Brown et al. |
| 5,690,619 A | 11/1997 | Erskine |
| 5,697,907 A | 12/1997 | Gaba |
| 5,700,250 A | 12/1997 | Erskine |
| 5,718,688 A | 2/1998 | Wozencroft |
| 5,755,699 A | 5/1998 | Blecher et al. |
| 5,795,339 A | 8/1998 | Erskine |
| 5,853,393 A | 12/1998 | Bogert |
| 5,879,337 A | 3/1999 | Kuracina et al. |
| 5,951,515 A | 9/1999 | Osterlind |
| 5,951,525 A | 9/1999 | Thorne et al. |
| 6,001,080 A | 12/1999 | Kuracina et al. |
| 6,004,294 A | 12/1999 | Brimhall et al. |
| 6,117,108 A | 9/2000 | Woehr et al. |
| 6,210,371 B1 | 4/2001 | Shaw |
| 6,221,047 B1 | 4/2001 | Greene et al. |
| 6,234,999 B1 | 5/2001 | Wemmert et al. |
| 6,379,333 B1 | 4/2002 | Brimhall et al. |
| 6,443,929 B1 | 9/2002 | Kuracina |
| 6,595,955 B2 | 7/2003 | Ferguson et al. |
| 6,629,959 B2 | 10/2003 | Kuracina et al. |
| 6,659,984 B2 | 12/2003 | Crawford et al. |
| 6,689,102 B2 | 2/2004 | Greene |
| 6,695,814 B2 | 2/2004 | Greene et al. |
| 6,743,186 B2 | 6/2004 | Crawford et al. |
| 6,749,588 B1 | 6/2004 | Howell et al. |
| 6,761,706 B2 | 7/2004 | Vaillancourt |
| 6,786,891 B2 | 9/2004 | Hiejima |
| 6,860,871 B2 | 3/2005 | Kuracina et al. |
| 6,881,202 B2 | 4/2005 | Coleman et al. |
| 6,976,976 B2 | 12/2005 | Doyle |
| RE38,996 E | 2/2006 | Crawford et al. |
| 6,997,902 B2 | 2/2006 | Thorne et al. |
| 7,125,397 B2 | 10/2006 | Woehr et al. |
| 7,144,387 B2 | 12/2006 | Millerd |
| 7,264,613 B2 | 9/2007 | Woehr et al. |
| 7,303,548 B2 | 12/2007 | Rhad et al. |
| 7,322,963 B2 | 1/2008 | Goh |
| 7,387,616 B2 | 6/2008 | Li |
| 7,611,499 B2 | 11/2009 | Woehr et al. |
| 7,811,261 B2 | 10/2010 | Rubinstein et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 8,100,858 B2 | 1/2012 | Woehr et al. |
| 8,235,945 B2 | 8/2012 | Baid |
| 8,251,950 B2 | 8/2012 | Albert et al. |
| 8,545,454 B2 | 10/2013 | Kuracina et al. |
| 8,556,853 B2 | 10/2013 | Vaillancourt |
| 2001/0047156 A1 | 11/2001 | Parker |
| 2002/0111566 A1 | 8/2002 | Crawford et al. |
| 2002/0169418 A1 | 11/2002 | Menzi et al. |
| 2003/0036731 A1 | 2/2003 | Wilkinson et al. |
| 2003/0105431 A1 | 6/2003 | Howell |
| 2003/0216687 A1 | 11/2003 | Hwang |
| 2003/0220587 A1 | 11/2003 | Swenson |
| 2003/0220612 A1 | 11/2003 | Hiejima |
| 2004/0049155 A1 | 3/2004 | Schramm |
| 2004/0049163 A1 | 3/2004 | Murashita |
| 2004/0167385 A1 | 8/2004 | Rioux et al. |
| 2004/0225262 A1 | 11/2004 | Fathallah et al. |
| 2005/0015054 A1 | 1/2005 | Chen |
| 2005/0119627 A1 | 6/2005 | Crawford |
| 2007/0100297 A1 | 5/2007 | Woehr et al. |
| 2008/0171986 A1 | 7/2008 | Baid |
| 2009/0131876 A1 | 5/2009 | Coyne |
| 2009/0163861 A1 | 6/2009 | Carlyon |
| 2009/0281499 A1 | 11/2009 | Harding et al. |
| 2010/0016804 A1 | 1/2010 | Muskatello et al. |
| 2010/0191188 A1 | 7/2010 | Harding et al. |
| 2010/0191189 A1 | 7/2010 | Harding et al. |
| 2010/0222746 A1 | 9/2010 | Burkholz |
| 2010/0249707 A1 | 9/2010 | Woehr et al. |
| 2012/0220956 A1 | 8/2012 | Kuracina et al. |

FOREIGN PATENT DOCUMENTS

| | | |
|---|---|---|
| DE | 3802353 A1 | 8/1989 |
| EP | 0443735 A1 | 8/1991 |
| EP | 0747085 A2 | 12/1996 |
| EP | 0749761 A1 | 12/1996 |
| EP | 0750916 A2 | 1/1997 |
| EP | 0826388 A2 | 3/1998 |
| EP | 0995459 A2 | 4/2000 |
| EP | 1291035 A2 | 3/2003 |
| EP | 1369142 B1 | 8/2005 |
| EP | 1604700 A1 | 12/2005 |
| EP | 2016964 A1 | 1/2009 |
| EP | 2075029 A1 | 7/2009 |
| FR | 2767480 A1 | 2/1999 |
| JP | H04102462 A | 4/1992 |
| JP | 2002248168 A | 9/2002 |
| JP | 2002330946 A | 11/2002 |
| JP | 2002539897 T | 11/2002 |
| WO | 9211885 A1 | 7/1992 |
| WO | 9908742 | 2/1999 |
| WO | 0057940 A1 | 10/2000 |
| WO | 0069501 | 11/2000 |
| WO | 0156642 A1 | 8/2001 |
| WO | 03011381 A1 | 2/2003 |
| WO | 2004043521 A1 | 5/2004 |
| WO | 2006096633 A1 | 9/2006 |
| WO | 2006096634 A1 | 9/2006 |
| WO | 2006096635 A1 | 9/2006 |
| WO | 2006096636 A1 | 9/2006 |
| WO | 2007022373 A2 | 2/2007 |

(56) References Cited

FOREIGN PATENT DOCUMENTS

| WO | 2010101573 A1 | 9/2010 |
|----|---------------|--------|
| WO | 2010110789 A1 | 9/2010 |
| WO | 2012075421 A1 | 6/2012 |

OTHER PUBLICATIONS

Desanto, Office Action Communication for U.S. Appl. No. 11/817,890 dated Oct. 11, 2012, 26 pages.
Final Office Action for U.S. Appl. No. 11/817,891, dated Jun. 9, 2015, 14 pages.
Office Action for U.S. Appl. No. 13/997,973, dated Mar. 12, 2015, 54 pages.
State Intellectual Property Office of the People's Republic of China, Notification of the First Office Action for Application No. CN 201180066317 dated Oct. 27, 2014, 19 pages.
Price, Notice of Allowance and Fee(s) Due for U.S. Appl. No. 11/817,892 dated Dec. 19, 2014, 71 pages.
Desanto, Notice of Allowance and Fee(s) Due for U.S. Appl. No. 11/817,890 dated Sep. 17, 2013, 17 pages.
Matney, Office Action Communication for U.S. Appl. No. 13/254,163 dated Oct. 15, 2013, 81 pages.
Omgba, Office Action Communication for U.S. Appl. No. 13/114,589 dated Oct. 31, 2013, 19 pages.
Patent Cooperation Treaty, Preliminary Report on Patentability and Written Opinion of the International Searching Authprity for PCT/US2012/032578 dated Oct. 8, 2013, 10 pages.
Erskine, Office Communication for U.S. Appl. No. 11/817,687 dated Dec. 9, 2010, 19 pages.
Erskine, Mexican Application No. MX/a/2007/010944, Office Action dated Mar. 11, 2011, 4 pages.
Erskine, Japanese Application No. JP07-5616-XY, Decision to Grant a Patent, dated Apr. 5, 2011, 6 pages.
Erskine, Taiwan Application No. 095107585, Office Action, dated Mar. 17, 2011, 3 pages.
Erskine, Mexian Application No. MX/a/2007/010946, Office Action, dated Apr. 2011, 2 pages.
Erskine, Japan Application No. P2008-500802, Notice of Reasons for Rejection, dated Apr. 5, 2011, 4 pages.
Erskine, China Application No. 201010109122.6, Office Action, dated Apr. 1, 2011, 11 pages.
Erskine, Office Action Communication for U.S. Appl. No. 11/817,892 dated Apr. 28, 2011, 25 pages.
Patent Cooperation Treaty, PCT Notification of Transmittal of International Preliminary Report on Patentability for PCT Application No. PCT/US06/07909 dated Aug. 16, 2007, 13 pages.
Erskine, Malaysia Application No. PI20071466, Office Action, dated Aug. 30, 2010, 3 pages.
Erskine, Taiwanese Application No. 095107587, Office Action dated Oct. 12, 2009, 12 pages.
Erskine, Australian Application No. 2006220691, Examiner's Report on Patent dated Jan. 19, 2009, 2 pages.
Erskine, Chinese Application No. 200680007484, Office Action dated Aug. 21, 2009, 13 pages.
Erskine, Taiwanese Application No. 095107585, Office Action dated Apr. 6, 2009, 9 pages.
Erskine, Taiwanese Application No. 095107585, Office Action dated Oct. 15, 2009, 7 pages.
European Patent Office, European Search Report for Application No. EP06737125, dated Feb. 10, 2010, 7 pages.
Erskine, Canadian Application No. 2,599,943, Office Action dated Dec. 30, 2010, 2 pages.
Erskine, Canadian Application No. 2,599,945, Notice of Allowance dated Nov. 25, 2010, 1 pages.
Erskine, Canadian Application No. 2,599,955, Office Action dated Dec. 21, 2010, 3 pages.
Erskine, Canadian Application No. 2,599,938, Office Action dated Dec. 20, 2010, 2 pages.
Erskine, Japanese Application No. P2008-500805, Final Office Action dated Jan. 25, 2011, 25 pages.
Erskine, Japanese Application No. P2008-500804, Notice to Grant dated Feb. 2, 2011, 6 pages.
Desanto, Office Action Communication for U.S. Appl. No. 11/817,890 dated Aug. 31, 2011, 33 pages.
Osinski, Notice of Allowance & Fee(s) Due for U.S. Appl. No. 11/817,687 dated Jun. 30, 2011, 8 pages.
Erskine, Mexican Application No. MX/a/2007/010943, Office Action dated Jun. 10, 2011, 2 pages.
Becamel, International Application No. PCT/US2009/036197, PCT International Preliminary Report on Patentability and Written Opinion of the International Searching Authority, Sep. 15, 2011, 10 pages.
Price, Office Action Communication for U.S. Appl. No. 11/817,892 dated Oct. 6, 2011, 14 pages.
Patent Cooperation Treaty, International Preliminary Report on Patentability and Written Opinion of the International Searching Authority for PCT/US2009/038246 dated Oct. 6, 2011, 7 pages.
Canadian Intellectual Property Office, Office Action for Application No. 2,599,943 dated Oct. 13, 2011, 2 pages.
IP Australia, Examiners First Report on Patent Application No. 2010203121 dated Nov. 4, 2011, 2 pages.
Patent Cooperation Treaty, Notification of Transmittal of the International Search Report and the Written Opinion of the International Searching Authority, or the Declaration for PCT/US2011/063118 dated Apr. 3, 2012, 17 pages.
Patent Cooperation Treaty, Notification of Transmittal of the International Search Report and the Written Opinion of the International Searching Authority, or the Declaration for PCT/US2011/063081 dated Mar. 22, 2012, 10 pages.
Desanto, Office Action Communication for U.S. Appl. No. 11/817,890 dated Apr. 30, 2012, 14 pages.
Patent Cooperation Treaty, Notification of Transmittal of the International Search Report and the Written Opinion of the International Searching Authority, or the Declaration for PCT/US12/32578 dated Aug. 3, 2012, 26 pages.
European Patent Office, European Search Report for EP12169737 dated Jul. 25, 2012, 4 pages.
European Patent Office, European Search Report for EP12169713 dated Jul. 26, 2012, 5 pages.
Omgba, Office Action Communication for U.S. Appl. No. 13/114,589 dated Sep. 14, 2012, 39 pages.
Flick: U.S. Appl. No. 13/259,715, filed Dec. 2, 2011, Office Action Dec. 17, 2012, 42pgs.
Shamsudin, Substantive/Modified Substantive Examination and Search Report, Application No. PI 2007146, Mar. 15, 2013, 4 pages.
Ehrsam, Supplementary European Search Report, Application No. EP 09 84 1250, Feb. 26, 2013, 5 pages.
Omgba, Office Action Correspondence, U.S. Appl. No. 13/114,589, Apr. 10, 2013, 15 pages.
Erskine, Australian IP Examination Report No. 2 dated Feb. 25, 2010, Reference No. 30355386/MRF/TLG/tzs, Application No. 2006220690, 2 pages.
Erskine, Canadian Application No. 2,599,943, Office Action dated Nov. 20, 2009, 2 pages.
Erskine, Chinese Application No. 200680007590, Office Action dated May 21, 2010, 4 pages.
Erskine, Australian Application No. 2006220691, Notice of Acceptance dated Jun. 9, 2010, 2 pages.
Erskine, Canadian Application No. 2,599,945, Office Action dated Nov. 13, 2009, 2 pages.
Erskine, Chinese Application No. 200680007484, Notification to Grant Patent Right dated Jun. 11, 2010, 4 pages.
Patent Cooperation Treaty, PCT/US06/07911, PCT International Search Report and Written Opinion, dated Jun. 23, 2006, 8 pages.
Patent Cooperation Treaty, PCT/US06/07911, PCT International Preliminary Report on Patentability, dated Feb. 12, 2007, 4 pages.
Erskine, U.S. Appl. No. 11/817,891, Office Communication dated Jun. 11, 2010, 11 pages.
Erskine, Australian Application No. 2006220692, Examiners First Report on Patent Application dated Oct. 21, 2008, 2 pages.
Erskine, Canadian Application No. 2,599,955, Office Action dated Mar. 5, 2010, 2 pages.
Erskine, Chinese Application No. 200680007485.0, Office Action dated Jun. 19, 2009, 6 pages.

(56) References Cited

OTHER PUBLICATIONS

Erskine, Chinese Application No. 200680007485.0, Notification to Grant Patent Right dated Jun. 4, 2010, 5 pages.
Erskine, Japanese Application No. P2008-500805, Office Action dated Apr. 20, 2010, 4 pages.
Erskine, Malaysia Application No. PI 20071465, Substantive Examination Report dated Apr. 30, 2010, 3 pages.
Patent Cooperation Treaty, PCT/US06/07912, PCT International Preliminary Report on Patentability, dated Sep. 20, 2007, 5 pages.
Patent Cooperation Treaty, PCT/US06/07912, PCT International Search Report and Written Opinion, dated Jun. 26, 2006, 8 pages.
Erskine, Taiwanese Application No. 095107584, Decision to Grant Patent dated Mar. 4, 2009, 5 pages.
Erskine, U.S. Appl. No. 11/817,687, Office Communication dated Jun. 30, 2010, 8 pages.
Erskine, U.S. Appl. No. 11/817,687, Office Communication dated Jan. 21, 2010, 9 pages.
Erskine, Australian Application No. 2006220689, Examiners First Report on Patent Application dated Jan. 15, 2009, 3 pages.
Erskine, Australian Application No. 2006220689, Patent Granted dated Jun. 18, 2010, 3 pages.
Erskine, Canadian Application No. 2,599,938, Office Action dated Feb. 23, 2010, 2 pages.
Erskine, Chinese Application No. 200680007548.2, Office Action dated Sep. 4, 2009, 4 pages.
Erskine, Chinese Application No. 200680007548.2, Notification to Grant Patent Right dated Jun. 12, 2010, 4 pages.
Erskine, Australian Application No. 2006220690, Notice of Acceptance dated Jun. 15, 2010, 3 pages.
Erskine, Japanese Application No. P2008-500802, Office Action dated Jun. 29, 2010, 6 pages.
Erskine, Malaysia Application No. PI 20071468, Substantive Examination Report dated Apr. 16, 2010, 2 pages.
Patent Cooperation Treaty, PCT/US06/07910, PCT International Preliminary Report on Patentability, dated Jul. 3, 2007, 20 pages.
Patent Cooperation Treaty, PCT/US06/07909, PCT International Search Report and Written Opinion, dated Jun. 26, 2006, 8 pages.
Erskine, Taiwanese Application No. 095107593, Decision to Grant Patent dated Dec. 11, 2009, 5 pages.
Patent Cooperation Treaty, PCT/US09/036197, PCT International Search Report and Written Opinion dated Apr. 28, 2009, 14 pages.
Patent Cooperation Treaty, PCT/US09/038246, PCT International Search Report and Written Opinion dated May 20, 2009, 11 pages.
Erskine, U.S. Appl. No. 11/817,891, Office Communication dated Oct. 19, 2009, 10 pages.
Erskine, Australian Application No. 2006220690, Examiner's First Report on Patent dated Nov. 11, 2008, 3 pages.
Erskine, Chinese Application No. 200680007590, Office Action (Translation) dated Aug. 21, 2009, 11 pages.
Erskine, European Application No. EP06737126, Supplementary European Search Report dated Feb. 11, 2010, 4 pages.
Patent Cooperation Treaty, PCT/US06/07910, PCT International Search Report and Written Opinion, dated Jul. 5, 2006, 8 pages.
Desanto, Office Action Communication for U.S. Appl. No. 11/817,890 dated Jun. 6, 2013, 19 pages.
Patent Cooperation Treaty, International Preliminary Report on Patentability for PCT/US2011/063081 dated Jun. 4, 2013, 7 pages.
Patent Cooperation Treaty, International Preliminary Report on Patentability for PCT/US2011/063118 dated Jun. 4, 2013, 8 pages.
European Patent Office, Intention to Grant for EP Application No. 06 737 126.0 dated Jun. 17, 2013, 92 pages.
Canadian Patent Office, Notice of Allowance for CA Application No. 2,599,943 dated Jul. 3, 2013, 1 page.
Price, U.S. Appl. No. 11/817,891, Non-Final Office Action, Sep. 16, 2014, 94 pgs.
Third Office Action for Chinese Patent Application No. 201180066325.4 dated Oct. 10, 2015, 7 pages. English language translation provided.
Office Action for Mexican Patent Application No. MX/a/2013/011676, 2 pages.
Office Action for JP Application No. 2014-504040, dated Jun. 30, 2015, 6 pages.
Office Action for CN Application No. 201180066317, dated Jun. 17, 2015, 5 pages.
Notice of Allowance and Fee(s) Due for U.S. Appl. No. 13/997,973, dated Jul. 31, 2015, 10 pages.
Notice of Allowance and Fee(s) Due for U.S. Appl. No. 11/817,891, dated Aug. 25, 2015, 14 pages.
Communication Pursuant to Article 94(3) EPC for EP Application No. 12169713.0, dated Aug. 4, 2015, 5 pages.
Second Office Action for CN Application No. 201180066325.4, dated Jun. 16, 2015, 7 pages.
Extended European Search Report for EP Application No. 11845646.6, dated Nov. 25, 2015, 10 pages.
Extended European Search Report for EP Application No. 11845959.3, dated Nov. 25, 2015, 9 pages.
Office Action for U.S. Appl. No. 14/110,352, dated Jan. 20, 2016, 95 pages.

NEEDLE SHIELD ASSEMBLY WITH HUB ENGAGEMENT MEMBER FOR NEEDLE DEVICE

CROSS REFERENCE TO RELATED APPLICATION

This patent application claims the benefit of U.S. Provisional Patent Application Ser. No. 61/418,997, filed Dec. 2, 2010.

TECHNICAL FIELD

The disclosure relates generally to needle devices, and more particularly, to a needle shield assembly including a hub engagement member that disengages the hub from the needle shield when the needle shield moves to a shielding position.

BACKGROUND OF THE INVENTION

Needle shielding devices come in a variety of forms that do not allow for easy and passive activation and disconnection from a hub, such as a catheter introducer hub. Furthermore, needle shielding devices protrude into the catheter introducer hub and occupy the volume of the female luer connector, thereby interfering with hemostatic valves and seals.

BRIEF DESCRIPTION OF THE INVENTION

A first aspect of the disclosure provides a needle device comprising: a hub; a needle having a longitudinal axis and a sharp distal end; and a needle shield assembly including: a needle shield movable between a non-shielding position and a shielding position, the needle shield preventing emergence of the sharp distal end of the needle therefrom in the shielding position; an engagement member slidingly disposed relative to the needle shield for engaging the hub to the needle shield in the non-shielding position; and a retainer operatively coupled to the engagement member and positioned to prevent disengagement of the engagement member from the hub in the non-shielding position, and enable removal of the hub from the needle shield by disengaging the engagement member from the hub when the needle shield moves to the shielding position.

A second aspect of the invention includes a needle shield assembly comprising: a needle shield movable between a non-shielding position and a shielding position, the needle shield preventing emergence of a sharp distal end of a needle therefrom in the shielding position; an engagement member slidingly disposed relative to the needle shield for engaging a hub to the needle shield in the non-shielding position; and a retainer operatively coupled to the engagement member and positioned to prevent disengagement of the engagement member from the hub in the non-shielding position, and enable removal of the hub from the needle shield by disengaging the engagement member from the hub when the needle shield moves to the shielding position.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

Figure 1:
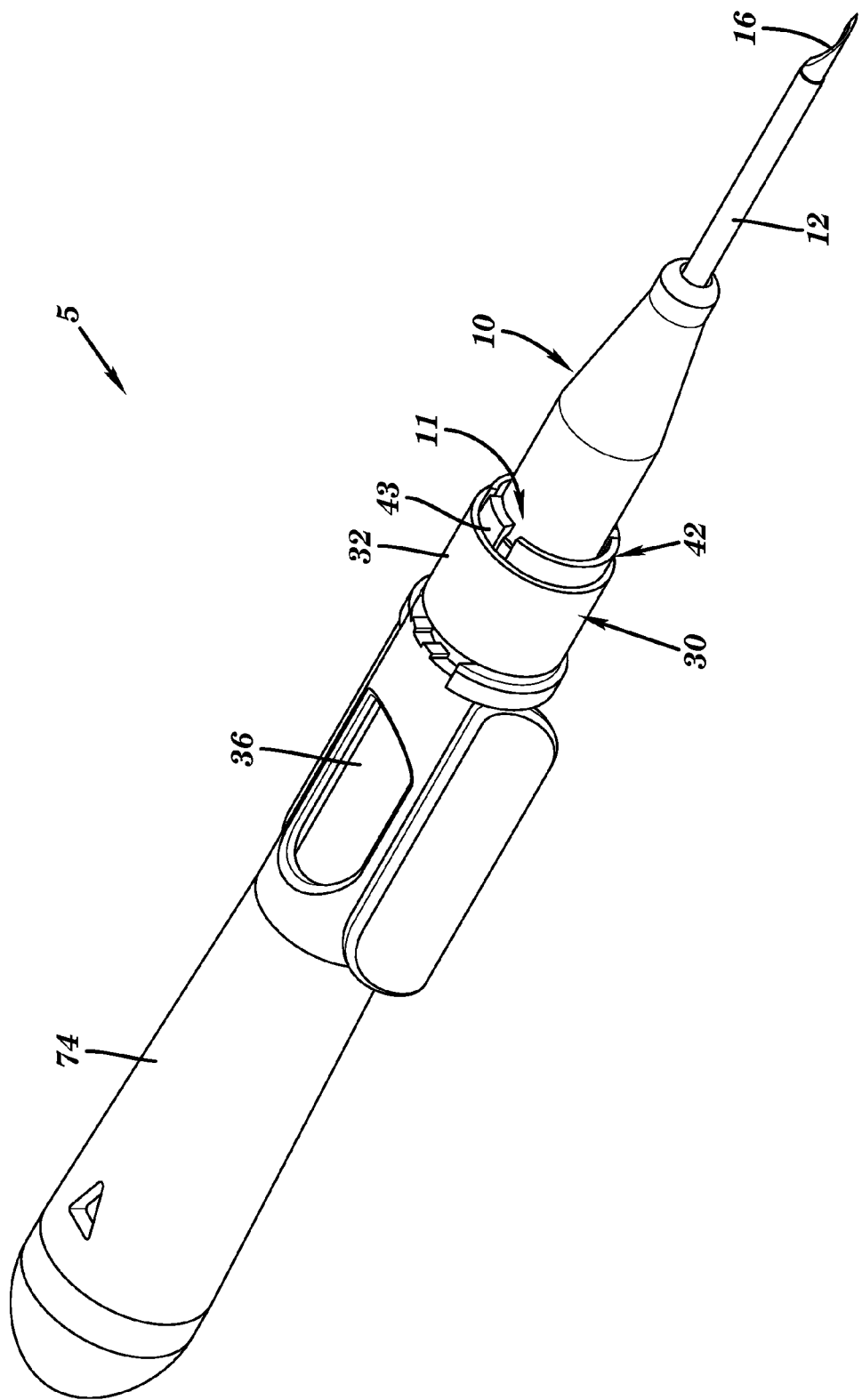
FIG. 1 shows a perspective view of a needle device including a needle shield assembly in a non-shielding position according to embodiments of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

Referring to the drawings, a needle device 5 including a needle shield assembly 30 according to embodiments of the invention is illustrated. In one embodiment, as illustrated, needle device 5 takes the form of a catheter introducer assembly including a catheter hub 10, a catheter cannula 12 and an introducer needle 14. However, needle device 5 is not limited to that form, and may include any device having a hub 10, such as a blood collection device, etc.

Figure 2:
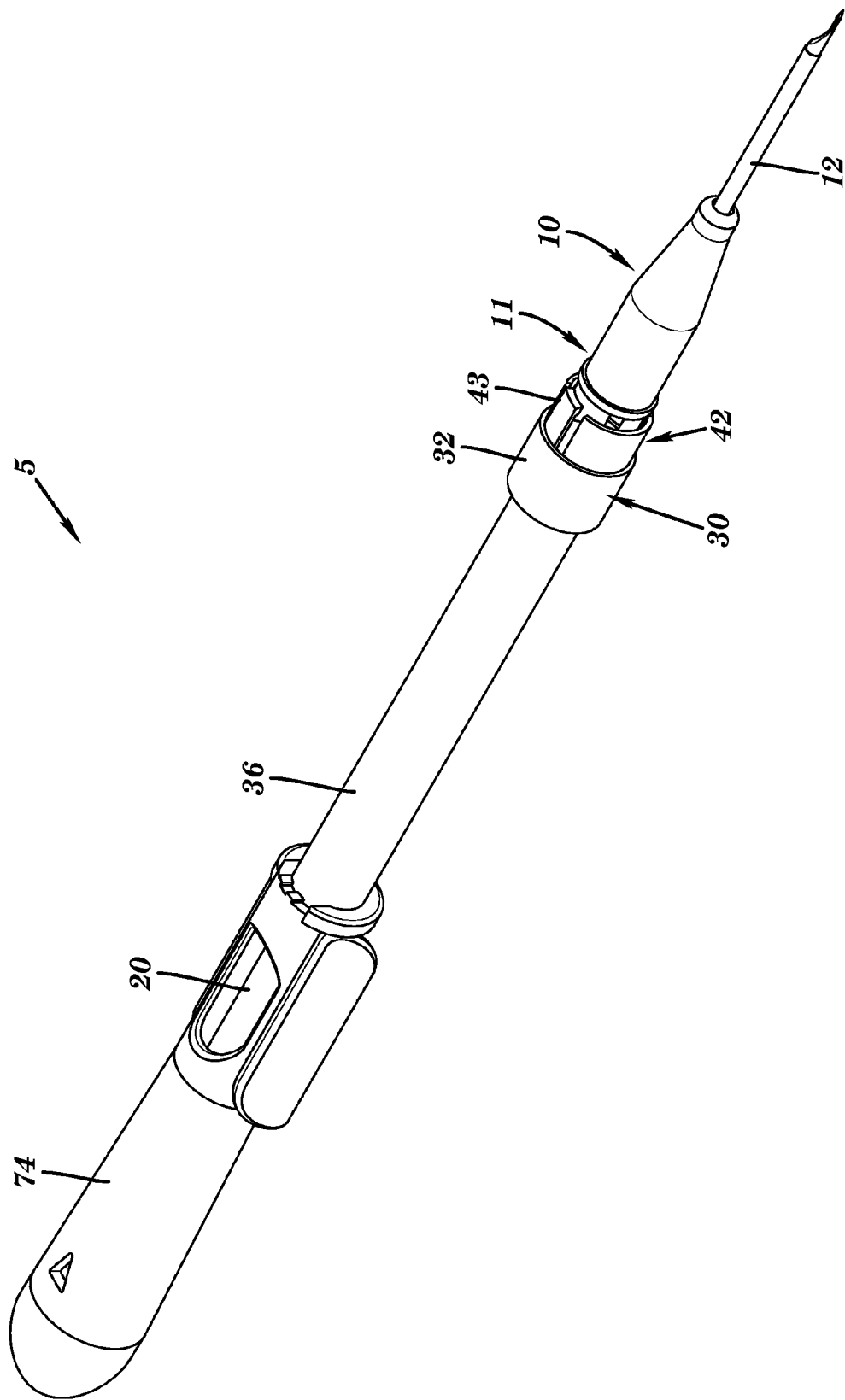
FIG. 2 shows a perspective view of a needle device including a needle shield assembly in a shielding position according to embodiments of the invention.
Figure 3:
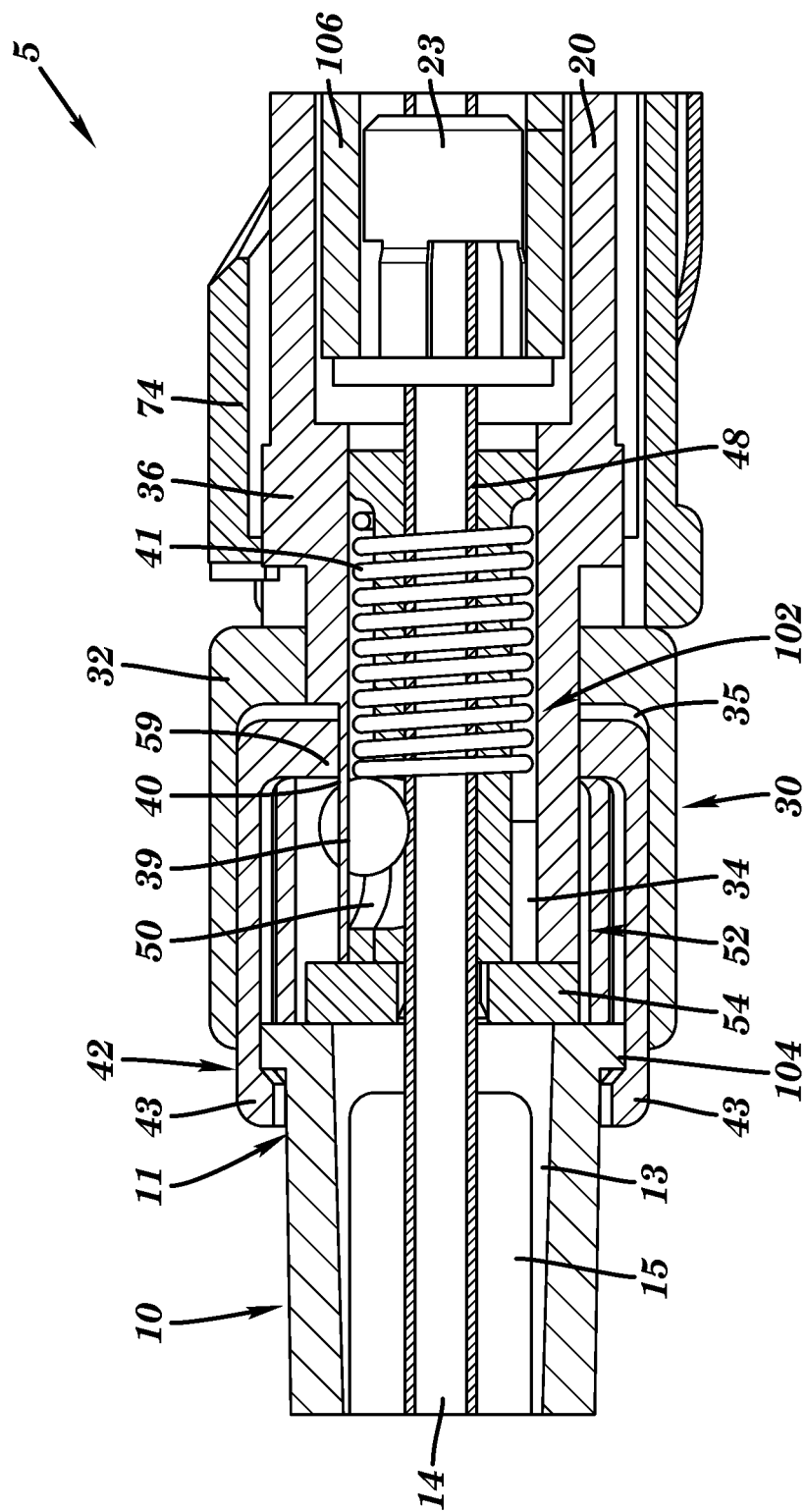
FIG. 3 shows a detailed cross-sectional view of the needle shield assembly and hub in a non-shielding position according to embodiments of the invention.
Figure 5:
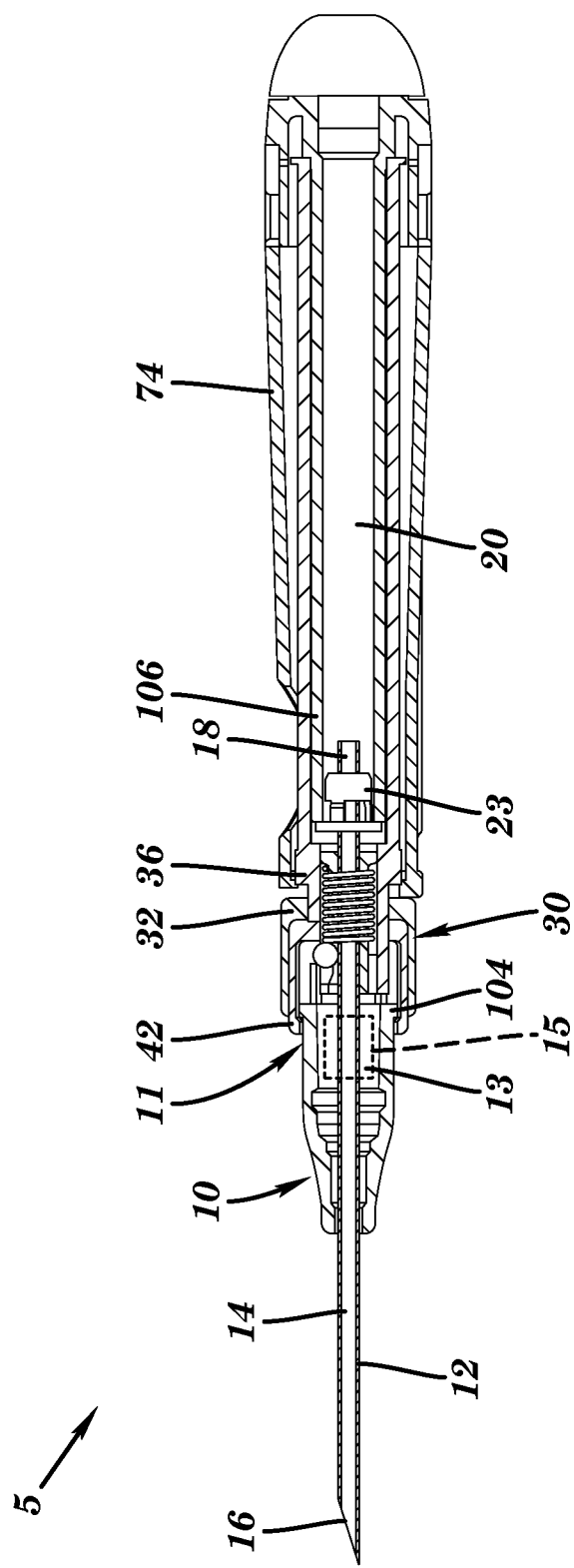
FIG. 5 shows a full cross-sectional view of a needle device including a needle shield assembly in a non-shielding position according to embodiments of the invention.
Figure 6:
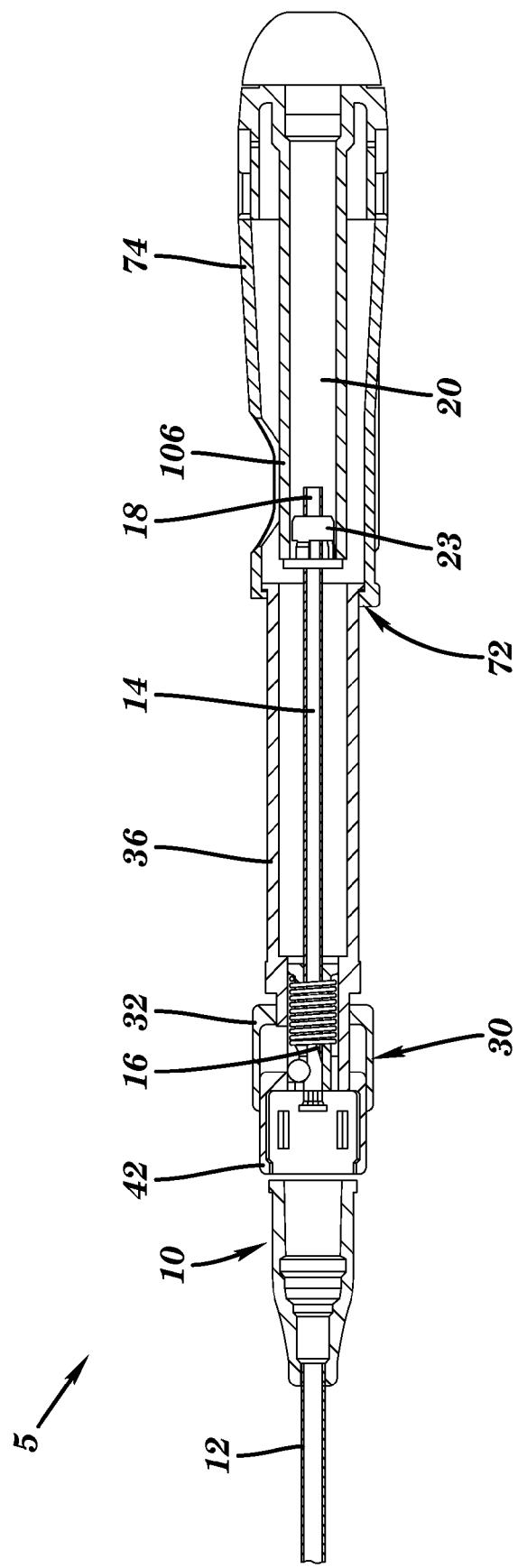
FIG. 6 shows a full cross-sectional view of a needle device including a needle shield assembly in a shielding position according to embodiments of the invention.

As shown best in FIGS. 1-3, needle device 5 includes a hub 10, a needle 14 (FIG. 3) and a needle shield assembly 30. A proximal end 11 of hub 10 may include a flanged portion 104 (FIG. 3); however, the flanged portion is not necessary in all instances. Hub 10 also may include a female luer adapter 13 into which a male component, such as a blood sealing device 15 (FIG. 3, phantom in FIG. 5) such as a valve or septum can be placed in hub 10. For example, needle shield assembly 30 may be located proximal to hub 10 to provide for a hemostatic valve. Although not shown, hub 10 may also include a port. Needle 14 includes a longitudinal axis, a sharp distal end 16 (FIG. 1) and a proximal end 18 (FIGS. 5-6). As shown in FIGS. 5 and 6, proximal end 18 can be secured to a distal end 106 of a needle hub 20, e.g., by glue, using a glue well 23, which is described in co-pending US Patent Application Publications Nos. 2009/0036843A1 and 2009/0032185A1, each of which are incorporated herein by reference. Needle hub 20 may be secured at its proximal end to a handle 74. As shown in FIG. 6, a stop flange 72 can be provided at a proximal end of sleeve 36 and a distal end of handle 74 to prevent distal movement beyond a shielding position, as described herein. Similar structures are shown in co-pending US Patent Application Publication Nos. 2008/0119795A1, 2009/0137958A1 and 2009/0249605A1, each of which are incorporated herein by reference. As described herein, proximal movement of needle hub 20 (via handle 74) retracts needle 14 into needle shield assembly 30, thereby moving a needle shield 102 from a non-shielding position (FIGS. 1, 3 and 5) to a shielding position (FIGS. 2, 4 and 6), and enables disconnection of hub 10 from needle shield 102. Needle 14, hub 10 and cannula 12 can be coaxial.

Figure 4:
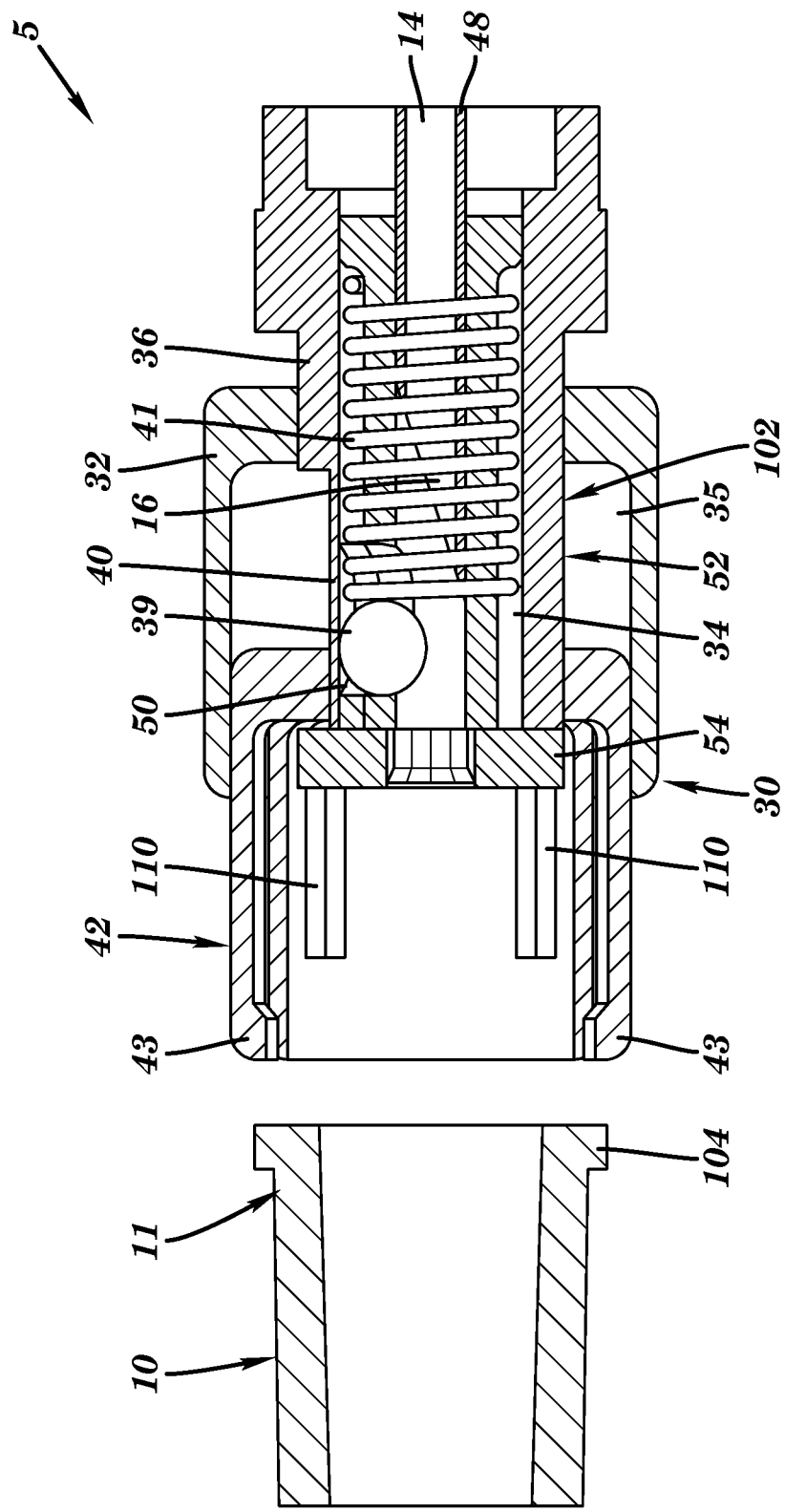
FIG. 4 shows a detailed cross-sectional view of the needle shield assembly and hub in a shielding position according to embodiments of the invention.

Referring to FIGS. 3 and 4, needle shield assembly 30 includes a needle shield 102, an engagement member 42 and a retainer 32.

Needle shield 102 is movable between a non-shielding position (FIG. 3) and a shielding position (FIG. 4). In the shielding position, needle shield 102 prevents emergence of sharp distal end 16 of needle 14 therefrom. In one embodiment, needle shield 102 includes a sleeve 36 adjacent to hub 10 (sleeve 36 may abut proximal end 11 of hub 10 or enter luer 13) and a carrier 34 for carrying a needle blocking object 39. Needle blocking object 39, although shown as a ball, may take a variety of other forms, e.g., cylinder, etc. As illustrated, carrier 34 is positioned at least partially in sleeve 36 and includes an internal (axial) lumen 48 dimensioned such that needle 14 can slide therewithin. Carrier 34 could be formed integral with sleeve 36, if desired. As described in co-pending U.S. patent application Ser. No. 11/817,890, filed Sep. 6, 2007, which is hereby incorporated by reference, and as shown in FIG. 4, carrier 34 may include a channel 50 or other structure for limiting radial movement of needle blocking object 39, in the shielding position of needle shield 102, to the longitudinal axis of needle 14 against the bias of a spring 41. In this illustrative embodiment, channel 50 is shaped and dimensioned so that needle blocking object 39 can be carried and can move along channel 50 and drop into place, at least partially across lumen 48, thereby blocking emergence of sharp distal end 16 of needle 14. Sleeve 36 is slidable with respect to handle 74 and needle hub 20 and may include a transparent material to allow blood flash back to be seen (see FIGS. 1 and 2). As shown in FIG. 3, sleeve 36 also includes a radial opening 40 extending through a wall of the sleeve through which needle blocking object 39 extends to engage, e.g., a distal edge 59, of an engagement member 42 in the non-shielding position. That is, needle blocking object 39 partially protrudes through radial opening 40 in sleeve 36 to abut distal edge 59 of engagement member 42. Consequently, engagement member 42 cannot move distally out of retainer 32 in the non-shielding position. Engagement member 42 also cannot move proximally due to its abutment with sleeve 36 and/or retainer 32. Although a particular embodiment of needle shield 102 has been described herein, it is emphasized that the teachings of the invention are not limited to any particular type of needle shield. Other needle shields also may be used such as a clip that snaps over the end of the needle (sometimes referred to as an introcan needle shield), or those with a different type of needle blocking object or different type of needle blocking object motion.

As shown in FIGS. 3 and 4, engagement member 42 is slidingly disposed relative to needle shield 102. As shown in FIG. 3, engagement member 42 engages hub 10 to needle shield 102 in the non-shielding position. In one embodiment, hub 10 includes a substantially circular portion (e.g., proximal end 11), and engagement member 42 engages with a segment of a circumference of the substantially circular portion. In one embodiment, engagement member 42 includes at least one engaging element 43 for engaging proximal end 11 of hub 10 to needle shield 102 in the non-shielding position. In one embodiment, engaging element(s) 43 are in the form of fingers that engage a flanged portion 104 of hub 10. Each engagement element(s) 43 may be referred to as a hook in this instance. Each engaging element 43 may be flexible, e.g., made of a polymeric material such as polycarbonate. Each engaging element 43 may form an arc-segment. Further, each engaging element 43 may be formed in a radially open position so each engaging element 43 moves away from hub 10 when engagement member 42 slides distally out of retainer 32. However, it is emphasized that a variety of other forms of engaging element(s) 43 are considered within the scope of the invention. Other engagement member 42 structure may include but is not limited to: a friction fit engagement, a male/female engagement, etc. Any number of engaging element(s) 43 may be employed. In the embodiment illustrated, sleeve 36 may assist in engaging the engaging element(s) 43 with proximal end 11 of hub 10 by including a flange 54 at a distal end 52 of sleeve 36 abutting proximal end 11, e.g., capturing proximal end 11 between engaging element(s) 43 and sleeve 36. However, flange 54 does not necessarily have to abut proximal end 11, and may enter luer 13 in some instances. In any event, flange 54 can have a radial dimension to avoid interaction with a plurality of ribs 110 (visible in FIG. 4), which act as a position stop for proximal end 11 of hub 10 as shown in FIG. 3. As noted herein, in the non-shielding position, longitudinal distal movement of engagement member 42 is constrained by needle blocking object 39. Similarly, longitudinal proximal movement of engagement member 42 is prevented by abutment of engagement member 42 with at least one of sleeve 36 or retainer 32 in the non-shielding position.

As shown in FIG. 3, retainer 32 is operatively coupled to engagement member 42 and positioned to prevent disengagement of engaging element(s) 43 from proximal end 11 of hub 10 in the non-shielding position. As shown in FIG. 4, retainer 32 enables removal of hub 10 from needle shield 102 by disengaging engagement member 42 (e.g., engaging element(s) 43) from hub 10 when needle shield 102 moves to the shielding position. Retainer 32 may be substantially cylindrical and surround sleeve 36, forming an annular space 35. Engagement member 42 is slidingly engaged on sleeve 36 in annular space 35 between sleeve 36 and retainer 32.

In operation, as observed by comparing FIGS. 3 and 4, retainer 32 enables removal of hub 10 from needle shield 102 by longitudinal distal movement of engagement member 42 relative to retainer 32 when needle shield moves to the shielding position, i.e., after retraction of needle 14 to allow needle blocking object 39 to partially enter internal axial lumen 48 of carrier 34. To deploy needle shield assembly 30, a user pulls handle 74 and thus needle hub 20 in a proximal direction, thus drawing needle 14 along catheter cannula 12 and carrier 34, until it stops due to the interaction of flange 72. At that point, sharp distal end 16 of needle 14 has passed needle blocking object 39 which has moved partially into internal lumen 48, urged there by spring 41. Needle blocking object 39 blocks the path of sharp distal end 16 should needle 14 move in the distal direction. Movement of needle blocking object 39 to the shielding position (FIG. 4) also substantially simultaneously releases engagement member 42 so that it can move distally out from retainer 32, thereby allowing engagement member 42 (e.g., engaging element(s) 43) to disengage from hub 10.

As noted herein, prior to proximal longitudinal retraction of needle 14 using handle 74, the longitudinal distal movement of engagement member 42 is prevented by engagement of engagement member 42 with needle blocking object 39 in the non-shielding position. Engagement member 42, e.g., engaging element(s) 43, engage hub 10 to lock needle shielding assembly 30 to hub 10. Without the radial restraint of retainer 32, engagement member 42, e.g., flexible engaging element(s) 43, will release easily from hub 10. However, once needle shield 102 enters the shielding position, shown in FIG. 4, retainer 32 no longer encloses engagement member 42, i.e., engaging element(s) 43. Consequently, with a slight exertion of force (e.g., in proximal direction), engagement member 42 can be disengaged from hub 10. At the same time, needle 14 is prevented from emerging from needle shield 102 by needle blocking object 39. Engagement member 42 slides along sleeve 36, but removal from needle shield 102 in the shielding position is prevented by flange 54 on a distal end of sleeve 36. Such activation happens automatically and passively as handle 74 is withdrawn proximally until needle shield assembly 30 detaches from hub 10.

Retainer 32, engagement member 42, carrier 34, sleeve 36, spring 41 (unless a non-coil spring is used) and handle 74 may all be coaxial. In one embodiment, sleeve 36 may be formed integrally with retainer 32. In addition, carrier 34 could be integral with sleeve 36. Since needle shield assembly 30 is substantially outside hub 10 in the shielding position, it provides space within hub 10 for a blood sealing device 15, for example a septum or a valve, as well as a side port (not shown), if desired. Each of the parts of needle device 5, excepting needle 14, may be made of appropriate plastic material. As noted above, engagement member 42 may be made or include portions that are made of flexible material.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A needle device comprising:
   a hub;
   a needle having a longitudinal axis and a sharp distal end; and
   a needle shield assembly including:
      a needle shield movable between a non-shielding position and a shielding position, the needle shield preventing emergence of the sharp distal end of the needle therefrom in the shielding position;
      an engagement member slidingly disposed relative to the needle shield for engaging an outer surface of the hub to the needle shield in the non-shielding position; and
      a retainer to in direct engagement with the engagement member and positioned to prevent disengagement of the engagement member from the hub in the non-shielding position, and enable removal of the hub from the needle shield by disengaging the engagement member from the hub when the needle shield moves to the shielding position.

2. The needle device of claim 1, wherein the needle shield includes a sleeve adjacent to the hub in the non-shielding position.

3. The needle device of claim 2, wherein the engagement member is positioned to slide along the sleeve, and removal of the engagement member from the needle shield in the shielding position is prevented by a flange on a distal end of the sleeve.

4. The needle device of claim 2, wherein the engagement member is slidingly engaged on the sleeve in an annular space between the sleeve and the retainer.

5. The needle device of claim 2, wherein the sleeve includes a transparent material.

6. The needle device of claim 2, wherein the sleeve is integral with the retainer.

7. The needle device of claim 1, wherein the needle shield includes a carrier for carrying a needle blocking object, the carrier including an internal lumen through which the needle extends.

8. The needle device of claim 7, wherein the carrier includes means for limiting radial movement of the needle blocking object, in the shielding position of the needle shield, to the longitudinal axis of the needle against the bias of a spring.

9. The needle device of claim 7, wherein the needle shield includes a sleeve having a radial opening extending through a wall of the sleeve through which the needle blocking object extends to engage an internal edge of the engagement member in the non-shielding position.

10. The needle device of claim 1, wherein the retainer enables removal of the hub from the needle shield by disengaging the engagement member from the hub when the needle shield moves to the shielding position by longitudinal distal movement of the engagement member relative to the retainer.

11. The needle device of claim 10, wherein the longitudinal distal movement of the engagement member is prevented by engagement of the engagement member with a needle blocking object in the non-shielding position.

12. The needle device of claim 1, wherein the engagement member includes at least one engaging element for engaging the hub.

13. The needle device of claim 12, wherein the at least one engaging element includes a hook for engaging a flanged portion of the hub.

14. The needle device of claim 13, wherein the at least one engaging element is flexible.

15. The needle device of claim 1, further comprising a needle hub coupled to a proximal end of the needle such that proximal movement of the needle hub retracts the needle into the needle shield assembly, thereby moving the needle shield from the non-shielding position to the shielding position.

16. The needle device of claim 15, further comprising a handle coupled to the needle hub.

17. The needle device of claim 1, wherein the retainer enables removal of the hub from the needle shield substantially simultaneously with the needle shield moving to the shielding position.

18. The needle device of claim 1, wherein the hub includes a blood sealing device therein.

19. The needle device of claim 1, wherein the hub includes a catheter introducer assembly.

20. The needle device of claim 1, wherein the hub includes a blood collection tube.

21. The needle device of claim 1, wherein the hub includes a substantially circular portion, and the engagement member engages with a segment of a circumference of the substantially circular portion.

22. A needle shield assembly comprising:
- a needle shield movable between a non-shielding position and a shielding position, the needle shield preventing emergence of a sharp distal end of the needle therefrom in the shielding position;
- an engagement member slidingly disposed relative to the needle shield for engaging an outer surface of a hub to the needle shield in the non-shielding position; and
- a retainer in direct engagement with the engagement member and positioned to prevent disengagement of the engagement member from the hub in the non-shielding position, and enable removal of the hub from the needle shield by disengaging the engagement member from the hub when the needle shield moves to the shielding position.

\* \* \* \* \*